(12) United States Patent
Rose et al.

(10) Patent No.: US 10,958,466 B2
(45) Date of Patent: Mar. 23, 2021

(54) ENVIRONMENTAL CONTROL SYSTEMS UTILIZING USER MONITORING

(71) Applicant: Plantronics, Inc., Santa Cruz, CA (US)

(72) Inventors: Marcus Dennis Rose, Miranda (AU); Evan Harris Benway, Santa Cruz, CA (US)

(73) Assignee: Plantronics, Inc., Santa Cruz, CA (US)

( * ) Notice: Subject to any disclaimer, the term of this patent is extended or adjusted under 35 U.S.C. 154(b) by 68 days.

(21) Appl. No.: 15/970,807

(22) Filed: May 3, 2018

(65) Prior Publication Data

US 2019/0342111 A1 Nov. 7, 2019

(51) Int. Cl.
*H04L 12/28* (2006.01)
*A61B 5/16* (2006.01)
*H04M 3/22* (2006.01)
*G10L 15/26* (2006.01)

(52) U.S. Cl.
CPC ............ *H04L 12/282* (2013.01); *A61B 5/165* (2013.01); *G10L 15/26* (2013.01); *H04M 3/2218* (2013.01)

(58) Field of Classification Search
CPC ...... H04L 12/282; A61B 5/165; G10L 15/265
See application file for complete search history.

(56) References Cited

U.S. PATENT DOCUMENTS

| | | | |
|---|---|---|---|
| 5,649,061 A | 7/1997 | Smyth | |
| 6,173,260 B1 * | 1/2001 | Slaney | G10L 17/26 704/250 |
| 7,120,880 B1 | 10/2006 | Dryer et al. | |
| 7,547,279 B2 | 6/2009 | Kim et al. | |
| 7,665,024 B1 * | 2/2010 | Kondziela | G06F 3/011 715/745 |
| 7,813,840 B2 | 10/2010 | Suyama et al. | |
| 10,013,977 B2 * | 7/2018 | Fu | G06F 17/2735 |
| 2003/0107478 A1 | 6/2003 | Hendricks et al. | |
| 2005/0200476 A1 | 9/2005 | Forr et al. | |
| 2007/0113725 A1 | 5/2007 | Oliver et al. | |
| 2007/0121824 A1 | 5/2007 | Agapi et al. | |

(Continued)

FOREIGN PATENT DOCUMENTS

| | | |
|---|---|---|
| JP | 2001282975 A | 10/2001 |
| JP | 2005143629 A | 6/2005 |
| JP | 2006293766 A | 10/2006 |

OTHER PUBLICATIONS

Adam Conner-Simons; Rachel Gordon, "Detecting emotions with wireless signals", MIT News, , MIT, retrieved at URL: http://news.mit.edu/2016/detecting-emotions-with-wireless-signals-0920, Sep. 20, 2016, 4 pages.

(Continued)

*Primary Examiner* — Vincent H Tran
(74) *Attorney, Agent, or Firm* — Chuang Intellectual Property Law

(57) ABSTRACT

Methods and apparatuses for environmental control systems are described. In one example, a method includes monitoring a voice communications call between a local call participant located in a building space and a remote call participant. The method includes detecting a change in a user state of the local call participant from the voice communications call. The method further includes adjusting an environmental parameter in the building space responsive to detecting the change in the user state of the local call participant.

14 Claims, 10 Drawing Sheets

(56) References Cited

U.S. PATENT DOCUMENTS

| | | |
|---|---|---|
| 2007/0165812 A1 | 7/2007 | Lee et al. |
| 2008/0167878 A1 | 7/2008 | Hause et al. |
| 2009/0002178 A1* | 1/2009 | Guday ................ A61B 5/0002 340/573.1 |
| 2009/0086940 A1* | 4/2009 | Diethorn ............ H04L 12/2827 379/102.05 |
| 2009/0125303 A1* | 5/2009 | Tachibana ............... H03G 3/32 704/226 |
| 2010/0309434 A1 | 12/2010 | Van Schijndel et al. |
| 2011/0201960 A1 | 8/2011 | Price et al. |
| 2012/0013750 A1 | 1/2012 | Heise |
| 2012/0303366 A1* | 11/2012 | Hetherington .......... G10L 25/87 704/233 |
| 2012/0317038 A1* | 12/2012 | Erbey ................. H04M 3/5183 705/304 |
| 2013/0019187 A1 | 1/2013 | Hind et al. |
| 2013/0081541 A1 | 4/2013 | Hasenoehrl et al. |
| 2014/0067130 A1 | 3/2014 | Pillai et al. |
| 2014/0119564 A1 | 5/2014 | Caskey et al. |
| 2014/0214973 A1* | 7/2014 | DeLuca ................. H04L 51/26 709/206 |
| 2014/0277649 A1 | 9/2014 | Chong et al. |
| 2014/0288939 A1* | 9/2014 | Beaurepaire ....... G01C 21/3655 704/276 |
| 2014/0378083 A1* | 12/2014 | Kannappan .......... H04W 76/50 455/404.1 |
| 2015/0081066 A1 | 3/2015 | Yeh et al. |
| 2015/0084518 A1* | 3/2015 | Takahashi .......... H05B 37/0236 315/152 |
| 2015/0206413 A1 | 7/2015 | Warner |
| 2015/0222989 A1 | 8/2015 | Labrosse et al. |
| 2015/0287421 A1 | 10/2015 | Benway et al. |
| 2016/0089955 A1* | 3/2016 | Ham .................. B60H 1/00742 165/202 |
| 2016/0162807 A1* | 6/2016 | Smailagic ............... G06N 3/006 706/12 |
| 2016/0179075 A1* | 6/2016 | Shin ....................... H04W 4/70 700/275 |
| 2016/0234595 A1 | 8/2016 | Goran et al. |
| 2016/0323668 A1* | 11/2016 | Abraham ................. H04R 1/02 |
| 2016/0351181 A1* | 12/2016 | Benway ................. H04K 3/825 |
| 2017/0053068 A1 | 2/2017 | Pillai et al. |
| 2017/0079558 A1 | 3/2017 | Bazemore et al. |
| 2017/0221484 A1* | 8/2017 | Poltorak ............... G10L 13/033 |
| 2017/0286037 A1* | 10/2017 | Sizelove ................. G06F 3/14 |
| 2017/0325718 A1* | 11/2017 | Boesen ................ A61B 5/1101 |
| 2017/0330208 A1* | 11/2017 | Wakako ................ G06Q 30/06 |
| 2017/0354231 A1* | 12/2017 | Okumura ............... A45D 34/02 |
| 2018/0073761 A1* | 3/2018 | Iuchi ........................ G06T 7/70 |
| 2019/0171409 A1* | 6/2019 | Boulanger ........... G10H 1/0066 |

OTHER PUBLICATIONS

Unknown, "Biometric Monitoring, Alerting, Reporting, and Analysis of Contact Center Agents", *IP.com Prior Art Database; IP.com Journal*, Aug. 13, 2013, 2 pages, IP.com No. IPCOM000230019D.

Jorn Bakker; Mykola Pechenizkiy; Nataklia Sidorova, "What's your current stress level? Detection of stress patterns from GSR sensor data." in *2011 IEEE 11th international conference on data mining workshops*, IEEE, 2011. pp. 573-580.

Unknown, "Real-time Measurement of Biometric Data using a Headset," product offering information provided by IPI Singapore (http://www.ipi-singapore.org) on about Jul. 18, 2015 (1 page).

\* cited by examiner

Voice Call Data 21

| Local User Unique ID 1 702 | | | |
|---|---|---|---|
| Location 1 704 | | | |
| Date 706 | Time 708 | Local User Speech Level (dB) 710 | Remote User Speech Level (dB) 712 |
| Date 1 | Time 1 | LUSL 1 | RUSL 1 |
| Date 2 | Time 2 | LUSL 2 | RUSL 2 |
| Date 3 | Time 3 | LUSL 3 | RUSL 3 |
| Date 4 | Time 4 | LUSL 4 | RUSL 4 |
| , | , | , | , |
| , | , | , | , |

FIG. 7

User State Data 19

| Local User |||||
|---|---|---|---|
| Unique ID 1 802 |||||
| Location 1 804 |||||
| Date 806 | Time 808 | Incident 810 | User State 812 |
| Date 1 | Time 1 | None | Normal |
| Date 2 | Time 2 | Overtalk | Agitated |
| Date 3 | Time 3 | Excessive Instant Noise Level | Agitated |
| Date 4 | Time 4 | Excessive Avg. Noise Level | Agitated |
| . | . | . | . |
| . | . | . | . |

FIG. 8

ENVIRONMENTAL CONTROL SYSTEMS UTILIZING USER MONITORING

BACKGROUND OF THE INVENTION

As real estate utilization increases and offices become more densely populated, maintaining an optimal physical environment for employees is becoming an increasingly challenging problem. As employee density increases within a space, there is increased likelihood that employee well-being will decrease with resulting decreased productivity.

In the prior art, environmental control systems have been limited to traditional heating and air conditioning systems. However, these prior art solutions do not account for the current state of employees at an individual level and are limited in scope and adaptability to increase well-being. As a result, improved methods, apparatuses, and technologies for environmental control systems are needed.

BRIEF DESCRIPTION OF THE DRAWINGS

The present invention will be readily understood by the following detailed description in conjunction with the accompanying drawings, wherein like reference numerals designate like structural elements.

FIG. 7 illustrates a voice call data record generated and utilized by a user state determination application in one example.

FIG. 8 illustrates a user state data generated and utilized by a user state determination application in one example.

DESCRIPTION OF SPECIFIC EMBODIMENTS

Figure 1:
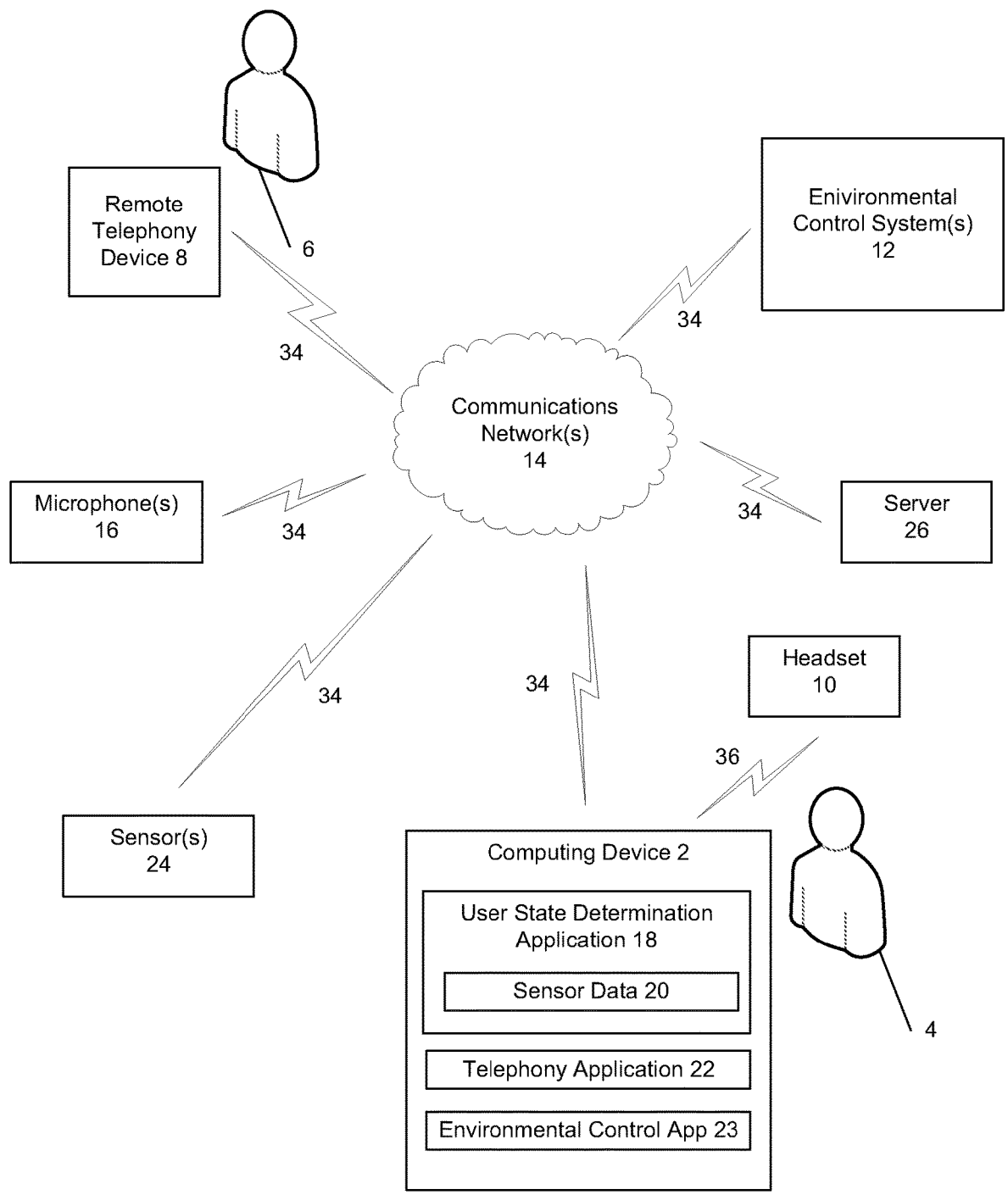
FIG. 1 illustrates a system for environmental control responsive to user state detection in one example.

Methods and apparatuses for environmental control systems utilizing user monitoring are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein.

Block diagrams of example systems are illustrated and described for purposes of explanation. The functionality that is described as being performed by a single system component may be performed by multiple components. Similarly, a single component may be configured to perform functionality that is described as being performed by multiple components. For purpose of clarity, details relating to technical material that is known in the technical fields related to the invention have not been described in detail so as not to unnecessarily obscure the present invention. It is to be understood that various example of the invention, although different, are not necessarily mutually exclusive. Thus, a particular feature, characteristic, or structure described in one example embodiment may be included within other embodiments unless otherwise noted.

The inventor has recognized certain limitations in current environmental control systems. In one example embodiment of the invention, a method includes monitoring a voice communications call between a local call participant located in a building space and a remote call participant. The method includes detecting a change in a user state of the local call participant from the voice communications call. The method further includes adjusting an environmental parameter in the building space responsive to detecting the change in the user state of the local call participant.

In one example embodiment, a system includes one or more microphones arranged to receive a local user speech from a local call participant during a voice communications call and output a microphone output signal, the local call participant located in a building space. The system includes one or more communications interfaces configured to receive during the voice communications call a received audio signal including a remote call participant speech from a remote call participant. The system includes one or more environmental control systems operable to adjust one or more environmental parameters in the building space. The system further includes one or more processors configured to monitor the voice communications call between the local call participant located in the building space and the remote call participant, detect a change in a user state of the local call participant from the voice communications call, and adjust an environmental parameter in the building space utilizing the one or more environmental control systems responsive to detecting the change in the user state of the local call participant.

In one example embodiment, a method includes receiving a user breath at a sensor disposed at a head worn device worn by a user in a building space. The method includes detecting a change in an emotional, physical, or neurological state of the user from the user breath received at the sensor disposed at the head worn device worn by the user. The method further includes adjusting an environmental parameter in the building space responsive to detecting the change in the emotional, physical, or neurological state of the head worn device user.

In one example embodiment, a method includes monitoring a sensor output from a sensor monitoring a user state in a building space. The method includes detecting a change in an emotional, physical, or neurological state of the user from the sensor output. The method further includes adjusting an environmental parameter in the building space responsive to detecting the change in the emotional, physical, or neurological state of the user.

In one example embodiment, an individual's and/or a group of individuals' emotional/physical/neurological state is analyzed and determined, and the surrounding environment is adapted. For example, environmental visuals, acoustics, scents, or temperature are adapted. The emotional/physical/neurological state is analyzed and determined based on data analytics from a number of sources, including voice analytics or odor and breath data from individuals via sensors. For example, individuals release different pheromones depending on their mood which is detected to identify the current user state. The overall vision for the solution utilizes sensors to detect a whole range of data within the office environment, including temperature, humidity, odor, air quality and user emotional state. The sensor data is captured and displayed on a floorplan wellness and productivity heat map. Advantageously, the environment is optimized for user productivity and wellness by adapting scent, audio, visual, temperature, or air quality parameters. For instance, mood enhancing scents (i.e., rosemary, citrus, coffee, etc.) that are adaptive are introduced depending on time of day and/or individuals' emotional/physical/neurological state. This may be done in conjunction with increasing oxygen levels, changing temperature in the surrounding area, and optimizing acoustic frequencies of sounds output in the environment. Advantageously, tapping into data provided by various sources allows identification of less than optimal zones within a monitored space and/or depreciation in individuals' emotional/physical/neurological state. These zones are modified with a view to increasing the individuals' well-being and productivity.

In one example, voice analytics during a voice call are leveraged to determine an individual's emotional, physical, and neurological state. For example, the voice analytics may include incoming acoustic levels, i.e., how loud incoming audio is at a decibel (dB) level. This may include identifying rapid increases in the incoming audio level, such as any loud shriek and/or sudden unexpected increase in decibel level dB at the listener's ear. For example, voice analytics are utilized to identify any noise above 90-95 dB to identify an undesirable user state and trigger an environmental response.

In a further example, transmit dB level from a microphone (e.g., a headset microphone) is monitored. The transmit dB level is utilized to identify when users are raising and or lowering their voice which is used to predict an individual's emotional, physical, and neurological state. For example, a raised voice indicates an argument is occurring and therefore the user has a negative emotional state. In a further example, voice call conversations are monitored and analyzed to identify on a voice call whether each participant is speaking and if they are speaking over each other (referred to as "over talk") or if there is silence on the call. For example, the over talk data is utilized to identify an argument is happening on the call and the user is therefore in an agitated state thereby triggering an environmental response. As used herein, the term "agitated state" refers to any undesirable, negative, or non-ideal emotional, physical, or neurological state.

In a further example, voice analytics are utilized to determine if the average noise level exceeds a predetermined noise dose for a given time period. For example, an undesirable user state is identified if the time weighted average over an 8 hour period exceeds 75 dBA, thereby triggering an environmental response.

FIG. 1 illustrates a system for environmental control responsive to user state detection in one example. The system includes computing device 2 and headset 10 proximate a local call participant 4. The system a remote telephony device 8 in proximity to a remote call participant 6. In one example, the system also includes a server 26, one or more environmental control system(s) 12, one or more microphone(s) 16, and one or more sensor(s) 24.

Each of the devices or systems shown in FIG. 1 is capable of communications with any other shown device or system via one or more communication network(s) 14 using network connections 34. Network connections 34 may be wired or wireless connections. In one example, a network connection 34 is a wired or wireless connection to the Internet. For example, computing device 2 includes a wireless transceiver to connect to an IP network via a wireless Access Point utilizing an IEEE 802.11 communications protocol. In one example, network connections 34 are wireless cellular communications links.

Local call participant 4 may utilize computing device 2 or the headset 10 in conjunction with the computing device 2 over wireless link 36 to transmit voice communications during a telephony call between local call participant 4 and remote call participant 6 conducted via communication network(s) 14. For example, communication network(s) 14 may include an Internet Protocol (IP) network, cellular communications network, public switched telephone network, IEEE 802.11 wireless network, Bluetooth network, or any combination thereof.

Computing device 2 may, for example, be any computing device, including without limitation a mobile phone, laptop, PDA, headset, tablet computer, or smartphone. In a further example, computing device 2 may be any device worn on a user body, including a bracelet, wristwatch, etc. Computing device 2 includes a user state determination application 18 interfacing with one or more of headsets 10, microphone(s) 16, sensor(s) 24, and remote telephony device 8 to receive data and identify a current user state, including a change in user state. In one example, user state determination application 18 stores sensor data 20 received from one or more of these devices. Computing device 2 also includes a telephony application 22 for voice calls and an environmental control application 23 for controlling one or more environmental control system(s) 12.

Figure 2:
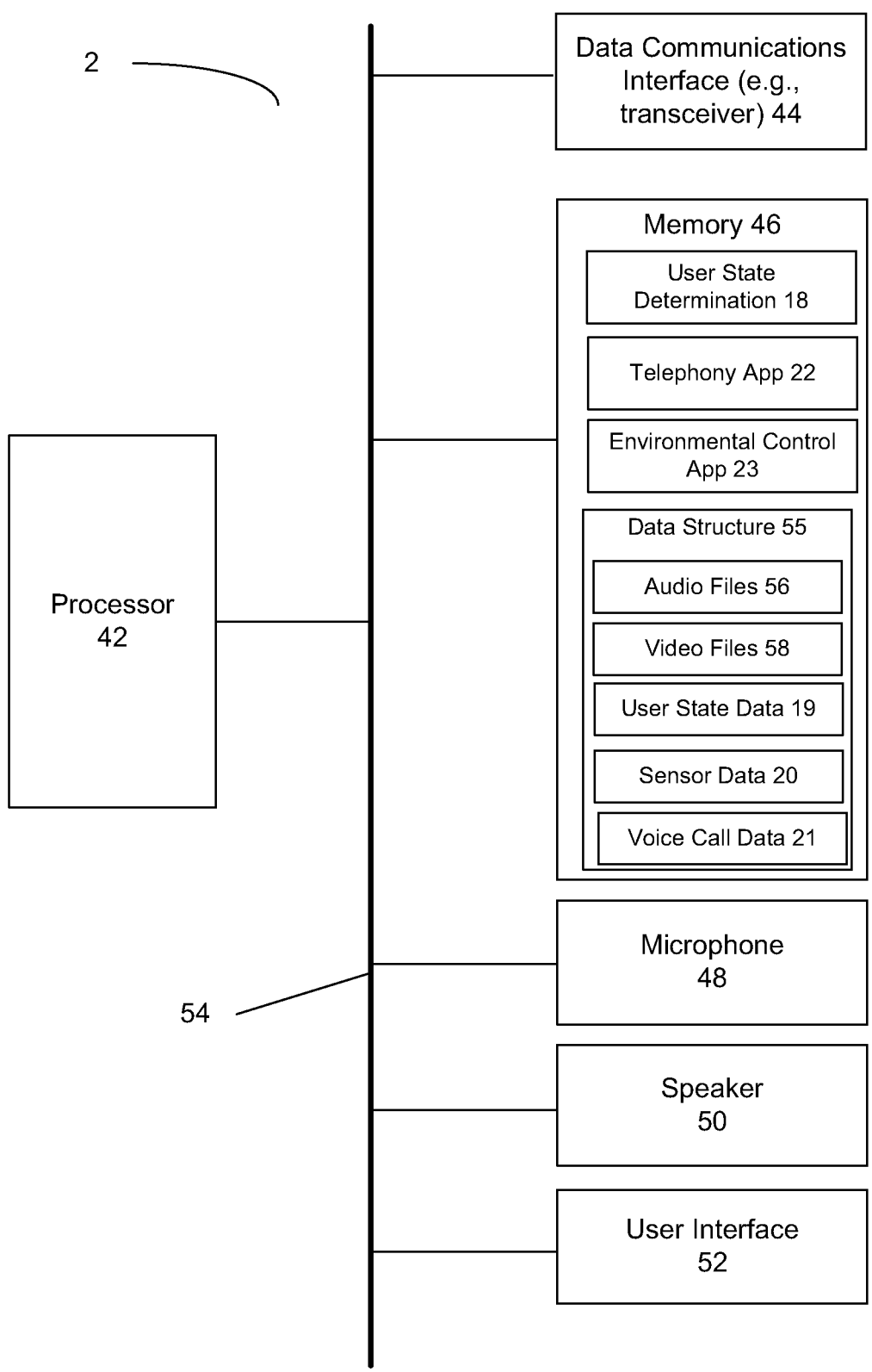
FIG. 2 illustrates a simplified block diagram of the computing device shown in FIG. 1 capable of performing user state determination and environmental control.

FIG. 2 illustrates a simplified block diagram of the computing device 2 shown in FIG. 1 capable of performing user state determination and environmental control. The computing device 2 includes a processor 42 operably coupled via an interconnect 54 to a data communications interface 44, memory 46, a microphone 48, a speaker 50, and a user interface 52. In one example, data communications interface 44 is a wireless communications transceiver (e.g., utilizing IEEE 802.11 communications).

Memory 46 stores a data structure 55 (e.g., a database, table, or any other file/memory structure) for storing applications and data described herein, including audio files 56, video files 58, user state data 19, sensor data 20, and voice call data records 21. Memory also stores user state determination application 18 and environmental control application 23 configured and operating as described herein, as well as telephony application 22. User state determination application 18, telephony application 22, and environmental control application 23 communicate data there between as needed to perform operations described herein. Although illustrated separately, user state determination application 18, telephony application 22, and environmental control application 23 may be into integrated into a single application. Furthermore, one or more operations performed by user state determination application 18, telephony application 22, and environmental control application 23 may be performed at and by applications at headset 10, or in conjunction with headset 10.

Memory 46 may include a variety of memories, and in one example includes SDRAM, ROM, flash memory, or a combination thereof. Memory 46 may further include separate memory structures or a single integrated memory structure. In one example, memory 46 may be used to store passwords, network and telecommunications programs, and/or an operating system (OS).

Processor 42, using executable code and applications stored in memory, performs the necessary functions associated with determining a user state and responsively controlling one or more environmental control systems within an environment such as a building open space as described herein. In one example, processor 42 further interacts with server 26 to receive audio files and video files. In one example, processor 42 is a high performance, highly integrated, and highly flexible system-on-chip (SoC), including signal processing functionality. Processor 42 may include a variety of processors (e.g., digital signal processors), with conventional CPUs being applicable. User interface 52 allows for manual communication between the system user (e.g., a system administrator) and the computing device.

Figure 3:
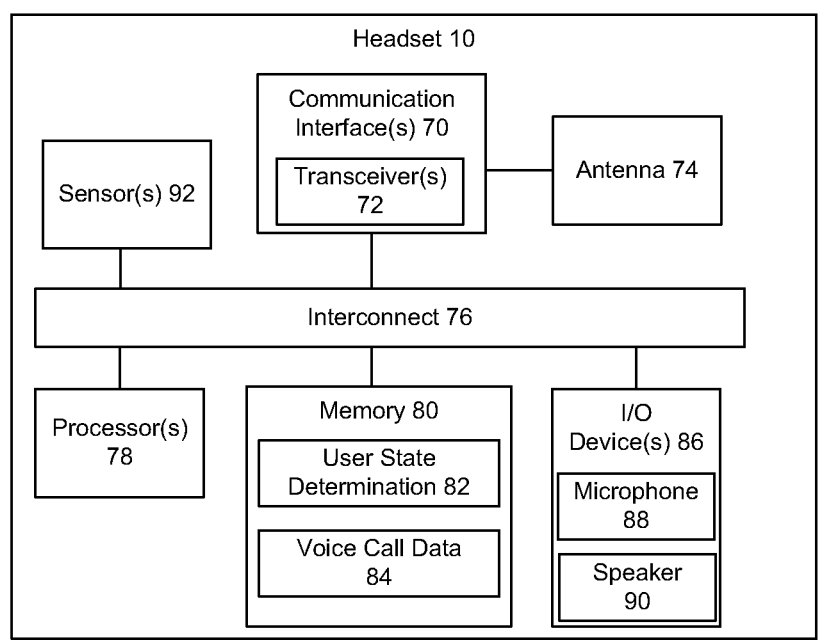
FIG. 3 illustrates a simplified block diagram of the headset shown in FIG. 1.

FIG. 3 illustrates a simplified block diagram of the headset 10 shown in FIG. 1. In one example, headset 10 may have the capability to communicate with other computer systems via a local or wide area network. Headset 10 includes communication interface(s) 70, antenna 74, memory 80, and I/O device(s) 86. Input/output (I/O) device(s) 86 are configured to interface with the user, and include a microphone 88 operable to receive a user voice input and a speaker 90 to output audio.

The headset 10 includes an interconnect 76 to transfer data and a processor 78 is coupled to interconnect 76 to process data. The processor 78 may execute a number of applications that control basic operations, such as data and voice communications via the communication interface(s) 70. Communication interface(s) 70 include wireless transceiver(s) 72 operable to communication with a communication interface(s) 44 at computing device 2. The block diagram shown for headset 10 does not necessarily show how the different component blocks are physically arranged on headset 10. For example, transceivers 72 may be separated into transmitters and receivers.

The communications interface(s) 70 may also include other processing means, such as a digital signal processor and local oscillators. Communication interface(s) 70 include one or more transceiver(s) 72. In one example, communications interface(s) 70 include one or more short-range wireless communications subsystems which provide communication between headset 10 and different systems or devices. For example, transceiver(s) 72 may be a short-range wireless communication subsystem operable to communicate with computing device 2 using a personal area network or local area network. The short-range communications subsystem may include one or more of: an infrared device and associated circuit components for short-range communication, a near field communications (NFC) subsystem, a Bluetooth subsystem including a transceiver, or an IEEE 802.11 (WiFi) subsystem in various non-limiting examples.

Headset 10 includes one or more sensor(s) 92, including sensors whose output is utilized to identify a user state. For example, sensor(s) 92 include a breath a sensor, an odor sensor, or a temperature sensor. In one example, an odor sensor such those available from Aromabit, Inc. is utilized. Sensor(s) 92 may be either worn on the user body or not worn on the user body and may rely on biofeedback. Sensor(s) 92 may rely on audio-visual cues or may identify the user state by transmitting and receiving reflected wireless signals. For example, a user heartbeat and/or breath may be monitored to identify a user emotional state or change in emotional state. Detection of an increased or rapid breath rate or increased heart rate may be used to identify an excited or agitated user state. Due to its worn state in proximity to the user skin and mouth, headset 10 is particularly advantageous to detecting the wearer's breath, odor, and/or temperature. In one example, sensor(s) 92 may include a don/doff sensor capable of detecting whether headset 10 is being worn on the user ear, including whether the user has shifted the headset from a not worn (i.e., doffed) state to a worn (i.e., donned) state. When headset 10 is properly worn, several surfaces of the headset touch or are in operable contact with the user. These touch/contact points are monitored and used to determine the temperature or donned/doffed state of the headset. In various examples, sensor(s) 92 may operate based on motion detection, temperature detection, or capacitance detection. For example, sensor(s) 92 is a capacitive sensor configured to detect whether it is in contact with user skin based on a measured capacitance.

The headset 10 includes a processor 78 configured to execute code stored in a memory 80. Processor 78 executes a user state determination application 82 to perform functions described herein. Although shown as separate applications, user state determination application 82 and user state determination application 18 may be integrated into a single application and located at one or both of computing device 2 or headset 10.

In one embodiment, headset 10 includes a user state determination application 82. Utilizing user state determination application 82, headset 10 is operable to determine a user state, including a change in user state, utilizing speech received at microphone 88 and/or voice call data 84 associated with a call between local call participant 4 and remote call participant 6. User state determination application 82 transmits the determined user state to computing device 2 or to server 26, depending upon the current connectivity mode of headset 10 to either communication network(s) 14 directly or to computing device 2 via link 36, as shown in FIG. 1.

Referring again to FIGS. 1 and 2, in one example operation, one or more microphones 42 at computing device 2 are arranged to receive a local user speech from a local call participant 4 during a voice communications call and output a microphone output signal, the local call participant 4 located in a building space under environmental control. In further examples, microphones 88 at headset 10 or microphone(s) 16 disposed may receive the local user speech from the local call participant. The one or more communications interfaces 44 at computing device 2 are configured to receive during the voice communications call a received audio signal including a remote call participant speech from a remote call participant 6. As shown in FIG. 1, one or more environmental control system(s) 12 are operable to adjust one or more environmental parameters in the building space. Computing device 2 monitors the voice communications call between the local call participant 4 located in the building space and the remote call participant 6, detects a change in a user state of the local call participant 4 from the voice communications call, and adjusts an environmental parameter in the building space utilizing the one or more environmental control system(s) 12 responsive to detecting the change in the user state of the local call participant 4.

In one example operation, user state determination application 18 detects the change in the user state from the voice communications call by detecting a change in a biological state of the local call participant 4. For example, the biological state may be emotional, physical, or neurological. Upon receiving notification from user state determination application 18 of the change in user state, environmental control application 23 adjusts the environmental parameter in the building space utilizing one or more of systems in environmental control system(s) 12 as described below.

In one example, user state determination application 18 monitors the voice communications call between the local call participant 4 located in the building space and the remote call participant 6 by monitoring the volume level of the speech of the local call participant 4. User state determination application 18 detects the change in the user state of the local call participant 4 from the voice communications call by detecting a change in the volume level of the speech of the local call participant 4.

In a further example, user state determination application 18 monitors the voice communications call between the local call participant 4 located in the building space and the remote call participant 6 by detecting a speech activity of the local call participant 4 and detecting a speech activity of the remote call participant 6. User state determination application 18 detects the change in the user state of the local call participant 4 from the voice communications call by detecting when the speech activity of the local call participant 4 occurs simultaneously with the speech activity of the remote call participant 6.

In a further example, user state determination application 18 monitors the voice communications call between the local call participant 4 located in the building space and the remote call participant 6 by detecting a speech activity of the local call participant 4 and detecting a speech activity of the remote call participant 6. User state determination application 18 detects the change in the user state of the local call participant 4 from the voice communications call by detecting when there is no speech activity of either the local call participant 4 or the remote call participant 6 for a predetermined duration of time.

Figure 5:
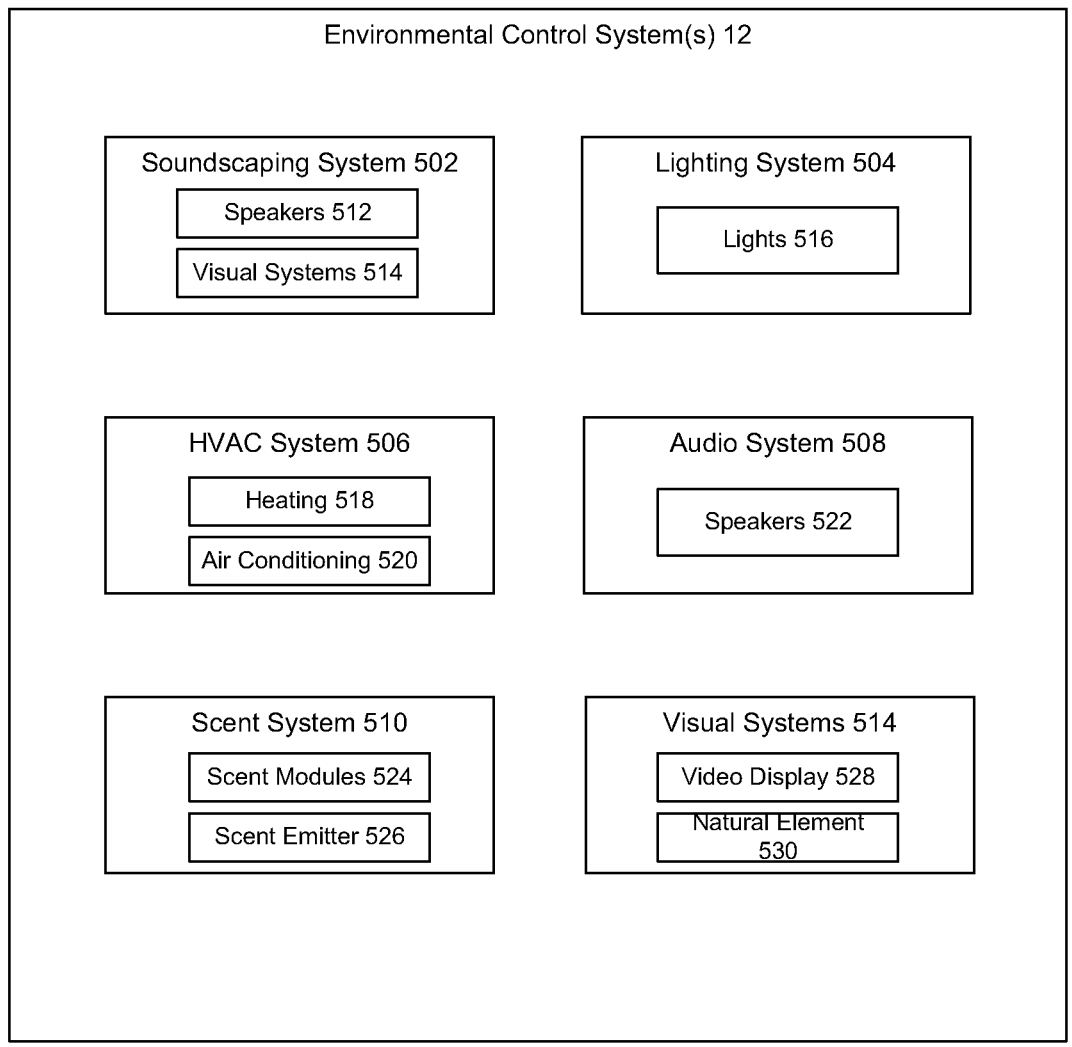
FIG. 5 illustrates environmental control system(s) in one example.

FIG. 5 illustrates environmental control system(s) 12 in one example. Environmental control system(s) 12 may include a soundscaping system 502 having loudspeakers 512 and visual systems 514. Soundscaping system 502 is described in further detail below. For example, soundscaping system 502 may increase output of nature sounds and show a matching visual on visual systems 514 (e.g., a video display) if it is detected the user state is agitated.

Environmental control system(s) 12 include a lighting system 504 including lights 516 arranged to output light within the building space. For example, lighting system 504 may decrease the brightness or change the color output to a more pleasant color if it is detected the user state is agitated.

Environmental control system(s) 12 include a heating, ventilation, or air conditioning (HVAC) system 506 including heating system 518 and air conditioning system 520. HVAC system 506 is arranged to adjust an ambient air temperature within the building space. For example, air conditioning system 520 may be used to decrease the ambient air temperature if it is detected the user state is agitated, such as an increase in body temperature is detected.

Environmental control system(s) 12 include an audio system 508 comprising one or more audio files and one or more loudspeakers 522 arranged to output the audio files in the building space. For example, audio system 508 may output desired music (e.g., relaxing classical music) if it is detected the user state is agitated.

Environmental control system(s) 12 include a scent emitting system 510 arranged to output a scent in the building space, the system 510 including one or more scent emitters 526 and scent modules 524. For example, scent emitting system 510 may initiate or adjust emission of floral scents such as lavender, roses, etc. if it is detected the user state is agitated.

Environmental control system(s) 12 include a visual systems 514 including a video display 528 and a nature element 530 arranged to display a visual within the building space. For example, visual systems 514 may display a nature scene such as video of a waterfall if it is detected the user state is agitated. Alternatively, nature element 530 is a physical natural waterfall that is activated or adjusted responsive to the user state.

Figure 4:
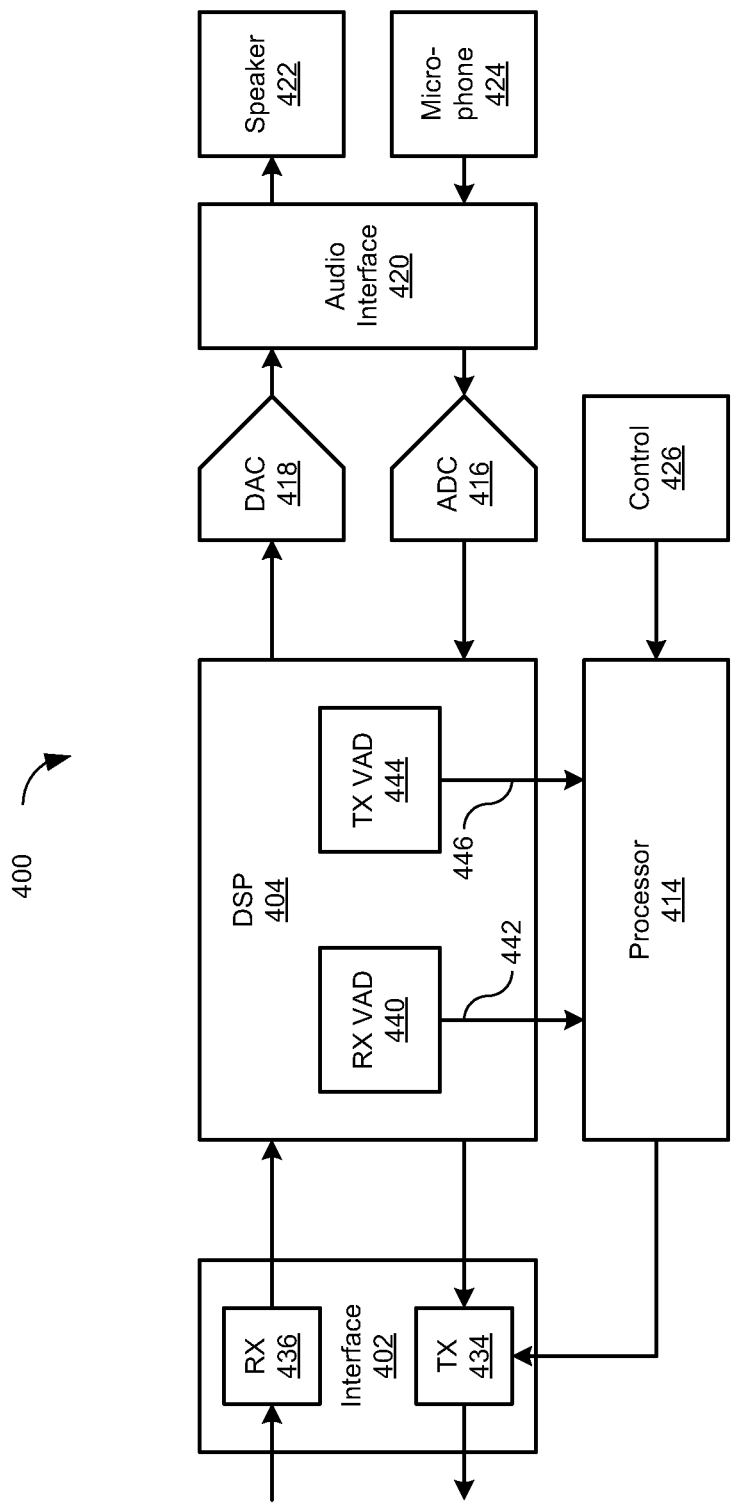
FIG. 4 shows processing elements for monitoring of voice communications between a local call participant and a remote call participant.

FIG. 4 shows processing elements 400 for monitoring of voice communications between the local call participant and the remote call participant by computing device 2 or headset 10 according to one embodiment. The illustrated elements may be implemented in hardware, software, or combinations thereof. As another example, various elements may be implemented as one or more digital signal processors or one or more integrated circuits. Referring to FIG. 4, the processing 400 includes a communications interface 402, a digital signal processor (DSP) 404, a processor 414, an analog-to-digital converter (ADC) 416, a digital-to-analog converter (DAC) 418, an audio interface 420, a speaker 422, a microphone 424, and a control 426.

For example, communications interface 402 may implement a wired or wireless communications protocol. The communications interface 402 may include a transmitter (TX) 434 and a receiver (RX) 436. The audio interface 420 may provide signal conditioning for audio provided to the speaker 422 and audio received from the microphone 424. The DSP 404 may perform volume detection and control, equalization, sample rate conversion, noise reduction, sound pressure limitation, and the like. The DSP 404 may include one or more voice activity detectors (VAD) and speech level detectors. In particular, the DSP 404 may include a receive voice activity detector (RX VAD) 440 and a transmit voice activity detector (TX VAD) 444. The RX VAD 440 may provide a signal 442 that indicates whether speech is present in the audio received from the communications interface 402. The TX VAD 444 may provide a signal 446 that indicates whether speech is present in the audio received from the audio interface 420. For example, each signal 442, 446 may be a binary signal, with one value representing the presence of speech and the other value representing the absence of speech. The signals 442, 446 of the VADS 440, 444 may be used by the processor 414 to determine the timing of the speech of the remote call participant and the timing of the speech of the local call participant. Processor 414 may determine the speech levels (including changes in speech levels) of the local call participant and remote call participant.

Figure 6:
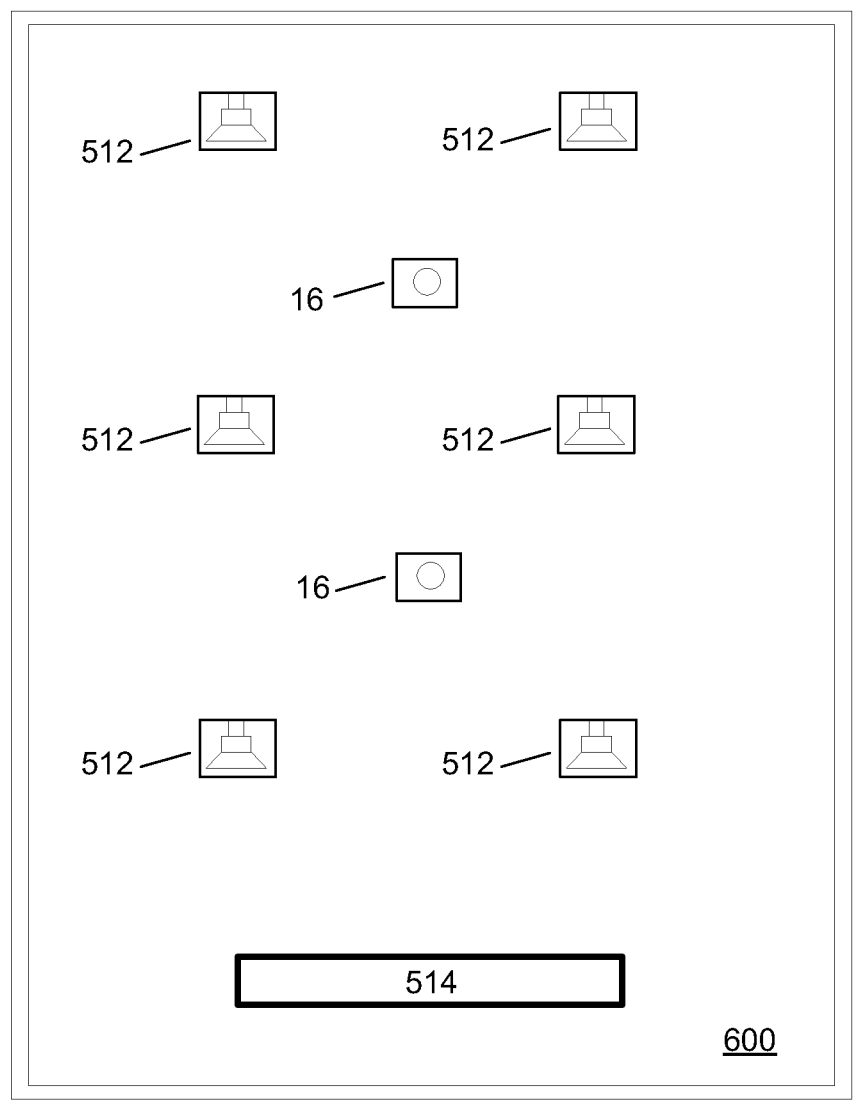
FIG. 6 illustrates a soundscaping system in one example.

FIG. 6 illustrates a soundscaping system 502 in one example. Soundscaping (also referred to as "sound masking") includes the introduction of soothing nature sounds (e.g., water sounds, rainforest sounds, birds chirping, etc.) in a space to reduce user agitation. It may also include the introduction of constant background noise in a space in order to increase acoustical comfort, reduce speech intelligibility, and increase speech privacy. For example, a pink noise, filtered pink noise, brown noise, or other similar noise may be injected into the open office in addition to the nature sounds. Pink noise is effective in reducing speech intelligibility, increasing speech privacy, and increasing acoustical comfort.

Soundscaping system 502 includes a plurality of loudspeakers 512, visual system(s) 514, and one or microphone(s) 16 under control of a computing device 2 or server 26 shown in FIG. 1. In a further example, computing device 2 interfaces with server 26 to receive control signals or vice versa.

Referring to FIG. 6, placement of loudspeakers 512 and microphone(s) 16 in a building space 600 is shown in one example. For example, building space 600 may be a large room of an office building. Computing device 2 is capable of electronic communications with each loudspeaker 512 and microphone 16 via either a wired or wireless communications link. For example, computing device 2 and loudspeakers 512 are connected via one or more communications networks such as a local area network (LAN) or an Internet Protocol network.

In one example, each loudspeaker 512 is network addressable and has a unique Internet Protocol address for individual control. Loudspeaker 512 includes a processor operably coupled to a network interface, output transducer, memory, amplifier, and power source. Loudspeaker 512 also includes a near-field wireless interface utilized to link with a control device such as computing device 2.

In one example, the network interface is a wireless transceiver and accompanying antenna for communications with a wireless router or access point. For example, the wireless transceiver is a Bluetooth or IEEE 802.11 transceiver. In a further example, the network interface is a wired interface, such as that an Ethernet jack used to connect to computing device 2 over the Internet or a local area network. The processor allows for processing data, including managing noise masking signals over the network interface, and may include a variety of processors (e.g., digital signal processors), with conventional CPUs being applicable.

In the system illustrated in FIG. 6, sound is output from loudspeakers 512 corresponding to a nature sound or a noise masking signal. The sound operates to decrease user agitation of a person in open building space 600. In one example, the output levels are advantageously dynamically adjusted in response to the detected user agitation state. In one example, output levels are adjusted on a speaker-by-speaker basis in order to address the location of a particular agitated user.

Visual systems 514 are arranged to be easily visible within the building space 600. In one example, visual systems 514 include a video display. In a further example, visual systems 514 may include in addition to or in alternative to the video display a water element system. In one example, the water element system is a floor-to-ceiling waterfall including an upper reservoir which receives water from a water supply, and a lower reservoir (e.g., a floor basin) to receive water which has fallen from the upper reservoir. The waterfall includes water recirculation tubes for recirculating water from the lower reservoir back to the upper reservoir, and a recirculation pump to recirculate the water through the recirculation tubes up to the upper reservoir. In one implementation, water falls from upper reservoir to the lower reservoir along the surfaces of one or more vertical glass panels disposed between the upper reservoir and the lower reservoir. To match the corresponding visual, the speaker sound may be the sound of a flow of water. In one example, the sound corresponding to the flow of water is a recording of a natural flow of water or an electronically synthesized sound of flow of water. In one example, the sound corresponding to a flow of water has been optimized to mask open space noise. For example, a recording of the flow of water used to generate sound has been processed to add 2-4 dB per octave higher frequency boost.

In response to user state reporting, soundscaping system 502 makes changes to the physical environment, including (1) increasing or reducing the volume of the sound soundscaping, (2) modifying the sound source—for example, from a filtered pink noise to the sound of running water, or (3) altering a visual displayed on visual systems 514.

FIG. 7 illustrates a voice call data record 21 generated and utilized by user state determination application 18 in one example. User state determination application 18 generates and stores a voice call data record 21 for each voice call by a local user (i.e., a local call participant). Voice call data record 21 may be a table identified by the local user ID 702 (e.g., an employee number) and include the user location 704 within the building space. Data record 21 includes the date 706, time 708, local call participant speech level 710, and remote call participant speech level 712 for the local user ID 702. In addition to local call participant speech levels 710 and remote call participant speech levels 712, any gathered or measured parameter derived from the voice call may be stored. For each voice call, the local call participant speech level 710 and remote call participant speech level 712 at periodic time intervals (e.g., every 250 ms to 1 second) is generated and measured, respectively, by and for use by user state determination application 18 as described herein. Data in one or more data fields in the table may be obtained using a database and lookup mechanism. In one example embodiment, user state determination application 18 utilizes voice call data record 21 to generate user state data 19 shown in FIG. 8.

FIG. 8 illustrates a user state data 19 generated and utilized by user state determination application 18 in one example. User state determination application 18 generates and stores a user state data 19 for each local user (i.e., a local call participant) utilizing, for example, voice call data record 21. User state data 19 may be a table identified by the local user ID 802 and include the user location 804 within the building space. For example, the environmental response may be localized to the user location 804. User state data 19 includes the date 806, time 808, identified incident 810, and identified user state 812. Identified incidents 810 may include, for example, over talk, excessive instantaneous noise levels, and excessive average noise levels during a voice call. For each identified incident 810, user state determination application 18 may determine the user state to be agitated. Data in one or more data fields in the table may be obtained using a database and lookup mechanism.

Figure 9:
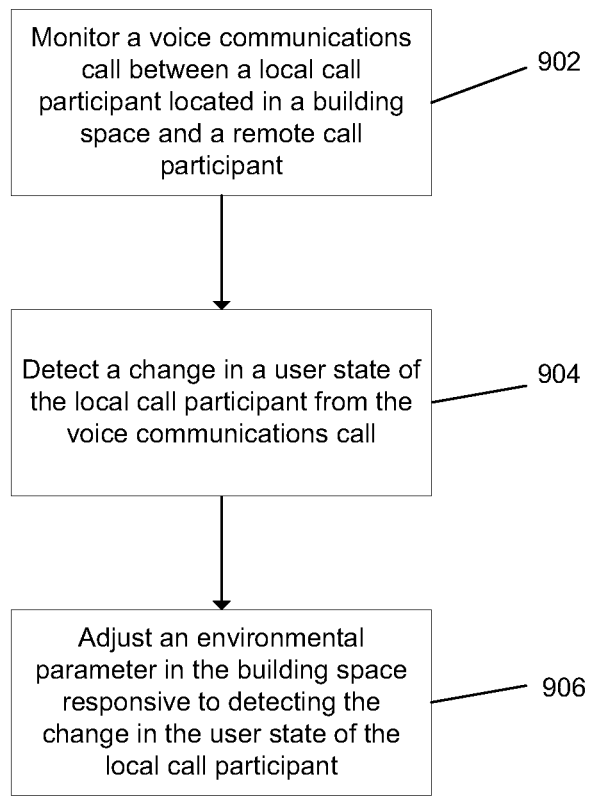
FIG. 9 is a flow diagram illustrating adjusting an environmental parameter based on user state in one example.

FIG. 9 is a flow diagram illustrating adjusting an environmental parameter based on user state in one example. At block 902, a voice communications call between a local call participant located in a building space and a remote call participant is monitored. At block 904, a change in a user state of the local call participant is detected from the voice communications call. In one example, detecting the change in the user state includes detecting a change in a biological state of the local call participant, such as an emotional, physical, or neurological state.

In one example, monitoring the voice communications call between the local call participant located in the building space and the remote call participant may include monitoring the volume level of the speech of the local call participant, and detecting the change in the user state of the local call participant from the voice communications call includes detecting a change in the volume level of the speech of the local call participant.

In a further example, monitoring the voice communications call between the local call participant located in the building space and the remote call participant includes detecting a speech activity of the local call participant and detecting a speech activity of the remote call participant, and detecting the change in the user state of the local call participant from the voice communications call includes detecting when the speech activity of the local call participant occurs simultaneously with the speech activity of the remote call participant.

In a further example, monitoring the voice communications call between the local call participant located in the building space and the remote call participant includes detecting a speech activity of the local call participant and detecting a speech activity of the remote call participant, and detecting the change in the user state of the local call participant from the voice communications call includes detecting when there is no speech activity of either the local call participant or the remote call participant for a predetermined duration of time.

At block 906, an environmental parameter in the building space is adjusted responsive to detecting the change in the user state of the local call participant. Adjusting the environmental parameter in the building space responsive to detecting the change in the user state of the local call participant may include, without limitation, one or more of the following (1) initiating or adjusting a scent output from a scent emitting device disposed in the building space, (2) adjusting an audio output from a loudspeaker disposed in the building space, (3) adjusting a video output from a display device disposed in the building space, (4) adjusting a temperature of the building space utilizing a heating, ventilation, or air conditioning control system, (5) adjusting a lighting output from one or more lights disposed in the building space, or (6) adjusting a sound masking noise output from a sound masking system disposed in the building space.

In various embodiments, the techniques of FIGS. 10-11 discussed below may be implemented as sequences of instructions executed by one or more electronic systems. For example, one or more electronic systems as shown in FIGS. 1-4 are utilized.

Figure 10:
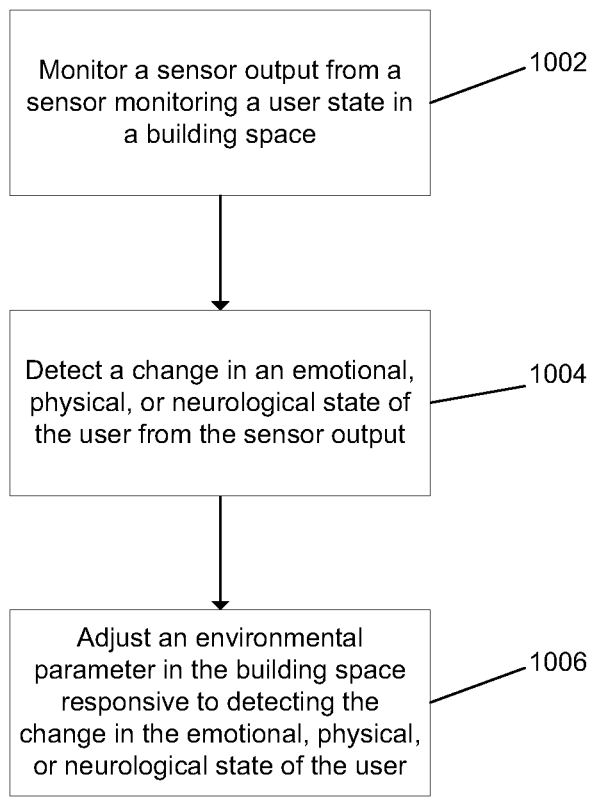
FIG. 10 is a flow diagram illustrating adjusting an environmental parameter based on user state in one example.

FIG. 10 is a flow diagram illustrating adjusting an environmental parameter based on user state in one example. At block 1002, a sensor output from a sensor monitoring a user state in a building space is monitored. At block 1004, a change in an emotional, physical, or neurological state of the user is detected from the sensor output. At block 1006, an environmental parameter in the building space is adjusted responsive to detecting the change in the emotional, physical, or neurological state of the user.

While the exemplary embodiments of the present invention are described and illustrated herein, it will be appreciated that they are merely illustrative and that modifications can be made to these embodiments without departing from the spirit and scope of the invention. Acts described herein may be computer readable and executable instructions that can be implemented by one or more processors and stored on a computer readable memory or articles. The computer readable and executable instructions may include, for example, application programs, program modules, routines and subroutines, a thread of execution, and the like. In some instances, not all acts may be required to be implemented in a methodology described herein.

Terms such as "component", "module", "circuit", and "system" are intended to encompass software, hardware, or a combination of software and hardware. For example, a system or component may be a process, a process executing on a processor, or a processor. Furthermore, a functionality, component or system may be localized on a single device or distributed across several devices. The described subject matter may be implemented as an apparatus, a method, or article of manufacture using standard programming or engineering techniques to produce software, firmware, hardware, or any combination thereof to control one or more computing devices.

Thus, the scope of the invention is intended to be defined only in terms of the following claims as may be amended, with each claim being expressly incorporated into this Description of Specific Embodiments as an embodiment of the invention.

What is claimed is:

1. A system comprising:
    one or more microphones arranged to receive a local call participant speech occurring within a building space from a local call participant during a voice communications call and output a microphone output signal, the local call participant located in the building space;
    one or more communications interfaces configured to receive during the voice communications call a received audio signal comprising a remote call participant speech occurring outside the building space from a remote call participant located at a remote location outside the building space;
    one or more environmental control systems operable to adjust one or more environmental parameters in the building space; and
    one or more processors configured to monitor the local call participant speech occurring within the building space and the remote call participant speech occurring outside the building space during the voice communications call, detect a change in a user state of the local call participant from the voice communications call utilizing the local call participant speech occurring within the building space and the remote call participant speech occurring outside the building space, and adjust an environmental parameter in the building space utilizing the one or more environmental control systems responsive to detecting the change in the user state of the local call participant from the voice communications call utilizing the local call participant speech occurring within the building space and the remote call participant speech occurring outside the building space.

2. The system of claim 1, wherein the one or more microphones are disposed on a headset worn by the local call participant.

3. The system of claim 1, wherein the one or more microphones are disposed proximate a ceiling area of the building space.

4. The system of claim 1, wherein the one or more environmental control systems comprise an audio system comprising one or more audio files and one or more loudspeakers arranged to output the one or more audio files in the building space.

5. The system of claim 1, wherein the one or more environmental control systems comprise a video system arranged to display a visual within the building space.

6. The system of claim 1, wherein the one or more environmental control systems comprise a scent emitting system comprising one or more scent emitters arranged to output a scent in the building space.

7. The system of claim 1, wherein the one or more environmental control systems comprise a heating, ventilation, or air conditioning system arranged to adjust an ambient air temperature within the building space.

8. The system of claim 1, wherein the one or more environmental control systems comprise a lighting system arranged to output light within the building space.

9. The system of claim 1, wherein the one or more processors are configured to detect the change in the user state from the voice communications call by performing operations comprising detecting a change in a biological state of the local call participant.

10. The system of claim 1, wherein the one or more processors are configured to adjust the environmental parameter in the building space responsive to detecting the change in the user state of the local call participant by performing operations comprising adjusting a video output from a display device disposed in the building space.

11. The system of claim 1, wherein the one or more processors are configured to adjust the environmental parameter in the building space responsive to detecting the change in the user state of the local call participant by performing operations comprising adjusting a sound masking noise output from a sound masking system disposed in the building space.

12. The system of claim 1, wherein the one or more processors are configured to monitor the local call participant speech occurring within the building space and the remote call participant speech occurring outside the building space during the voice communications call by performing operations comprising monitoring a volume level of the local call participant speech, and the one or more processors are configured to detect the change in the user state of the local call participant from the voice communications call by performing operations comprising detecting a change in the volume level of the local call participant speech.

13. The system of claim 1, wherein the one or more processors are configured to detect the change in the user state of the local call participant from the voice communications call utilizing the local call participant speech occurring within the building space and the remote call participant speech occurring outside the building space by performing operations comprising detecting when the local call participant speech occurring within the building space occurs simultaneously with the remote call participant speech occurring outside the building space.

14. A method comprising:
monitoring a voice communications call between a local call participant located in a building space and a remote call participant located outside the building space comprising monitoring a local call participant speech occurring within the building space and a remote call participant speech occurring outside the building space;
detecting a change in an emotional, physical, or neurological state of the local call participant from the voice communications call utilizing the local call participant speech occurring within the building space and the remote call participant speech occurring outside the building space; and
adjusting an environmental parameter in the building space responsive to detecting the change in the emotional, physical, or neurological state of the local call participant from the voice communications call utilizing the local call participant speech occurring within the building space and the remote call participant speech occurring outside the building space.

* * * * *